(12) United States Patent
Arai et al.

(10) Patent No.: US 6,376,716 B1
(45) Date of Patent: Apr. 23, 2002

(54) PROCESS FOR THE PREPARATION OF AROMATIC SULFUR COMPOUNDS

(75) Inventors: Isamu Arai; Tutomu Yamaguchi; Yoko Hida, all of Toda (JP)

(73) Assignee: Nippon Finechemical Co., Ltd., Tokyo (JP)

( * ) Notice: Subject to any disclaimer, the term of this patent is extended or adjusted under 35 U.S.C. 154(b) by 0 days.

(21) Appl. No.: 09/530,741

(22) PCT Filed: Jun. 30, 1999

(86) PCT No.: PCT/JP99/03514

§ 371 Date: May 4, 2000

§ 102(e) Date: May 4, 2000

(87) PCT Pub. No.: WO00/14060

PCT Pub. Date: Mar. 16, 2000

(30) Foreign Application Priority Data

| Sep. 9, 1998 | (JP) | 10-255305 |
| Oct. 19, 1998 | (JP) | 10-296944 |
| Feb. 23, 1999 | (JP) | 11-044448 |
| Feb. 23, 1999 | (JP) | 11-044449 |

(51) Int. Cl.⁷ ............................................. C07C 321/00
(52) U.S. Cl. .............................. 568/21; 568/29; 568/25; 568/61; 568/67
(58) Field of Search ............................... 568/21, 29, 25, 568/61, 62, 67, 56, 57, 38

(56) References Cited

U.S. PATENT DOCUMENTS

| 3,069,472 A | * 12/1962 | Loev et al. |
| 3,071,622 A | * 1/1963 | Laufer et al. |
| 3,071,625 A | * 1/1963 | Kulik et al. |
| 4,375,562 A | 3/1983 | Blank et al. |
| 5,650,542 A | 7/1997 | Fiege et al. |
| 5,741,933 A | 4/1998 | Goda et al. |
| 5,808,164 A | * 9/1998 | Shaw et al. ................... 568/44 |

FOREIGN PATENT DOCUMENTS

| EP | 0 316 942 A | 5/1989 |
| EP | 0 747 350 A | 12/1996 |
| JP | 8-143533 A | 6/1996 |
| JP | 9-40636 A | 2/1997 |

OTHER PUBLICATIONS

CA:114:101244 abs of J Chem Soc Chem Commun by Pitchumani et al (22) pp 1613–1614, 1990.*
Journal of American Chem Society vol. 74 by Tarbell et al pp 1862–1863, 1952.*
CA:79:125998 abs of Vestn. Mosk. Univ., Kim by Abdin et al 14(4) pp 491–3, 1973.*
Casreact:103:22225 abs of Synth Commun by Fristad et l 15(1) pp 1–5, 1985.*
Advanced Organic Chemistry : Reactions, Mechanisms, and Structure by Jerry March Mc Graw Hill pp 500, 1968.*
CA:88:135848 abs of Chem Lett (1) pp 13–14 and Kosugi 1978.*
Clarke, K., et al., "1,2–Benzisothiazoles. Part IV. 1 Preparation Of The 3–Methyl Derivative From O–Mercaptoacetophenone Oxime: A Re–Examination", *Journal of the Chemical Society*, vol. 4, 1973, pp. 356–359, ISSN:1472–7781.
Burawoy, A., et al., "O–Mercapto–Azo–Compound. Part IV. Preparation And Debenzylation Of 1-(2–Benzylthiophenylazo)–2–Napthol And 1-(1–Benzylthio–2–Naphthyl–Azo)–2–Napthol", *Journal of the Chemical Society*, 1954, pp. 82–90.

* cited by examiner

*Primary Examiner*—Jean F. Vollano
(74) *Attorney, Agent, or Firm*—Frishauf, Holtz, Goodman, Langer & Chick, P.C.

(57) ABSTRACT

A process for the preparation of an aromatic thiophenol represented by the formula (I): $Y_n$—Ar—$(SH)_m$(I), wherein Ar represents an aromatic hydrocarbon; Y represents at least one substituent bonded to a carbon atom constituting the aromatic ring of Ar, which substituent is selected from the group consisting of halogen, nitro, nitrile, sulfone, sulfamoyl and hydrocarbylsulfonyl groups; m is an integer of 1 or more; and n is an integer of 1 or more, which comprises (a) reacting an aromatic thioether represented by the formula (II): $Y_n$—Ar—$(SR)_m$(II), wherein R represents a monovalent secondary or tertiary hydrocarbyl, or a monovalent primary hydrocarbyl group represented by the formula: —$CH_2$—$R^1$ or —$CH_2$—$CR^2$=C $(R^2)_2$, wherein $R^1$ represents a monovalent aromatic ring group optionally substituted by a monovalent hydrocarbyl group, and each of $R^2$ is the same or different from each other and represents hydrogen or a monovalent hydrocarbyl group, with (A) a Lewis acid in the presence of a solvent or with a protonic acid, provided that when (A) is a protonic acid, R is not a primary hydrocarbyl group, and (b) optionally hydrolyzing the reaction product from step (a).

30 Claims, No Drawings

PROCESS FOR THE PREPARATION OF AROMATIC SULFUR COMPOUNDS

This is the national phase of PCT/JP99/03514, filed Oct. 30, 1999, now WO00/14060.

Process for the preparation of aromatic sulfur compounds

1. Technical Field

This invention relates to the preparation of aromatic thiols from aromatic thioethers, and also, relates to the preparation of aromatic disulfides via said aromatic thiols. The present invention further relates to the preparation of aromatic thiols via the above-mentioned aromatic thioethers obtained from aromatic halogeno-compounds, and the preparation of aromatic disulfides via said aromatic thiols.

2. Background Art

Aromatic thiols represented by the general formula (Ia):

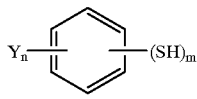

(Ia)

wherein Y represents chloro, bromo, iodo, nitro, nitrile, sulfone, sulfamoyl and hydrocarbylsulfonyl groups, each of which may be the same or different from each other; m is an integer of 1 to 6, n is 0 or an integer of 1 to 5, provided that m+n is 6 or less, and aromatic disulfides represented by the general formula (IIIa):

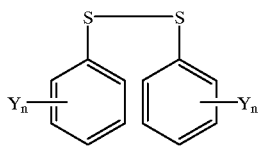

(IIIa)

wherein Y and n have the same meanings as defined above, have been used as an intermediates of medicines, agricultural chemicals, electronic materials, etc.

Some processes for the aromatic monothiols, aromatic dithiols or aromatic disulfides having such substituents have been proposed.

For example, in Kogyo Kagaku Zasshi, vol. 70, No. 8, pp. 114–118 (1967), the preparation of halogenated aromatic thiol which comprises reacting polychlorinated benzene with sodium hydrogen sulfate in liquid ammonia with autoclave to substitute one of the chlorine atom to a mercapto group is described. According to this method, halogenated aromatic thiol can be obtained in a high yield from polychloro benzene having 4 to 6 chlorine atoms, but the yield for dichlorothiophenol from trichlorobenzene is only 17 to 20% and also there are many problems and complexities to handle liquid ammonia and an industrial limitation due to the high pressure reaction with autoclave.

In Japanese Patent Publication No. 26100/1979, there is disclosed the preparation of halogenated aromatic thiol which comprises the reaction of halogenated aminoaromatic compound with sodium nitrite and conc. hydrochloric acid to form diazonium compound which reacts under reflux with potassium O-ethyldithiocarbonate and sodium hydroxide. This method is not preferred since it is not only complex but also dangerous to handle the diazonium salt.

In Japanese Provisional Patent Publication No. 156257/1981, there is disclosed the preparation of 3,5-dichlorothiophenols which comprises reacting 1,3,5-trichlorobenzene or 1-bromo-3,5-dichlorobenzene with alkali metal sulfide in a solvent such as diethylene glycol. This process gives objective compound with a relatively easy operation but the yield is low and many byproducts are formed so that the purification is difficult.

In Zhur. Org. Khim. vol. 11, p. 1132 (1975), there is disclosed the preparation of aromatic thiol by reacting halogenated aryl compound with hydrogen sulfide in the presence of thorium oxide, but the process requires high temperature (550° C. or higher) and the yield is not good.

In Japanese Provisional Patent Publication No. 48564/1990, there is disclosed the preparation of thiophenol by the introduction into a benzene ring having no nitro group of a diaryl sulfide, by the electrophilic substitution of the group such as halogeno, nitro group, etc. on the benzene ring of the diaryl sulfide having a nitro group at one of the benzene rings and then, the resulting compound is subjected to the exchange reaction with thiophenol in the presence of a basic substance such as sodium hydroxide whereby thiophenol the nucleus of which is substituted by said substituent can be obtained. However, this process is complex and it is not suitable when a lot of substituents is to be introduced into the benzene ring of the thiophenol.

In Japanese Provisional Patent Publication No. 72749/1986, there is disclosed the preparation of o-halothiophenols by the reaction of N,N-dialkylcarbamoyl halide with an o-halophenol to synthesize O-o-halophenyl-N,N-dialkylcarbamates, and the rearrangement reaction of S-o-halophenyl-N,N-dialkylcarbamate by heating, and hydrolysis of the resulting compound. However, this process is difficult of operation because of a complex multi-step reaction and passing through unstable carbamoyl halide. Also, the rearrangement reaction is carried out at high temperature whereby side reactions occur, and the process is particularly disadvantageous for the introduction of substituent except halogen.

There are disclosed the preparation of corresponding halogenated thiophenol by the reduction of 4-halobenzene sulfinic acid (in Japanese Provisional Patent Publication No. 295968/1990), 4-halobenzene sulfonyl chloride (in Japanese Provisional Patent Publication No. 181455/1991), and halobenzene sulfenyl halide (in Japanese Provisional Patent Publication No. 186418/1993), respectively, by the use of metal powder such as zinc powder with a mineral acid. However, this reduction is carried out in the presence of a mineral acid so that a specific apparatus is required.

In Japanese Provisional Patent Publication No. 140086/1993, there is disclosed the preparation of halothiophenol by the reaction of monohalobenzene with sulfur monochloride using a catalyst such as zinc chloride, and the reduction of the resulting product by a reducing agent such as zinc, etc. This process also consists of the reduction as mentioned above so that the same problems are involved.

In Japanese Provisional Patent Publication No. 182463/1992, there is disclosed a process for the preparation of halothiophenol by the reaction of poly-halobenzene with sulfide such as sodium hydrogen sulfide, sodium sulfide, potassium sulfide, etc. In these processes, the rate of the reaction is slow so that the formed aromatic thiol reacts with the halogenated benzene to give aromatic sulfide whereby the yield is low.

In Japanese Provisional Patent Publication No. 198162/1992, there is disclosed the preparation of halogenoaromatic thiol by the reaction of poly-halogenobenzene with thioglycolate. In Japanese Provisional Patent Publication No. 178816/1993, there is disclosed the preparation of halogenoaromatic thiol by the reaction of halogenated phenyl thioglycollic acid with sulfide such as sodium hydrogen sulfide or aromatic thiol with a base. But, highly pure aromatic thiol cannot be obtained with good yield by this process.

In Japanese Provisional Patent Publication No. 143533/1996, there is disclosed the preparation of halogenoaromatic thiol by the chlorination of the methyl group bound to the sulfur atom of thioanisol by chlorine gas and then the hydrolysis of the resulting halogenothioanisol. Moreover, in Japanese Provisional Patent Publication No. 143532/1996, there is disclosed that hydrolysis of the above-mentioned halogenated thioanisol is carried out in the presence of a mineral acid, and halogenated aromatic disulfide can be obtained by the oxidative dimerization of the halogenoaromatic thiol obtained by said hydrolysis with an oxidizing agent such as hydrogen peroxide, etc. However, in this process, methyl mercaptane which is volatile and stinks is used, and complex step of introducing a chlorine gas to chlorinate a methyl group is required. Incidentally, it has not yet been known about the reaction to prepare aromatic thiol from aromatic thioether in the presence of a Lewis acid by eliminating a hydrocarbyl group.

The object of this invention is to provide the preparation of highly pure aromatic thiols and disulfides with good yields from the substituted aromatic thioethers in benzene. Another object is to provide the preparation of highly pure aromatic thiols and disulfides having a substituent(s) from aromatic halogeno compounds by simple and easy operation with good yield.

The present inventors have studied to solve the above-mentioned problems, and as a result, they have found that a hydrocarbyl group of aromatic thioethers having specific hydrocarbyl group can be easily eliminated in the presence of a Lewis acid or a protonic acid, and the aromatic halogeno compounds are allowed to react with specific hydrocarbyl-mercaptide alkali metal salt and, if necessary, the resulting aromatic thioethers are decomposed by a Lewis acid or a protonic acid, whereby the objects can be accomplished and the present invention has completed.

DISCLOSURE OF THE INVENTION

That is, the present invention relates to the preparation of an aromatic thiol represented by the formula (I):

   (I)

wherein Ar represents an aromatic hydrocarbon residue;
Y represents at least one kind of substituent bonded to a carbon atom constituting the aromatic ring of Ar, which is selected from the group consisting of halogeno, nitro, nitrile, sulfone, sulfamoyl and hydrocarbylsulfonyl groups; m is an integer of 1 or more; and n is 0 or an integer of 1 or more, which comprises reacting an aromatic thioether represented by the formula (II):

   (II)

wherein R represents a monovalent secondary or tertiary hydrocarbyl group, or a monovalent primary hydrocarbyl group represented by the formula:

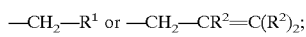

where $R^1$ represents a monovalent aromatic group which may be substituted by a monovalent hydrocarbyl group, and each of $R^2$ may be the same as or different from each other and represents hydrogen or a monovalent hydrocarbyl group;
Y, Ar, m and n have the same meanings as defined above,
in the presence of (A) a Lewis acid or a protonic acid provided that when the protonic acid is used, the primary hydrocarbyl group is excluded from R, and a solvent(s), and, if necessary, hydrolyzing the obtained reaction product.

The present invention also relates to the preparation of an aromatic disulfide represented by the formula (III):

   (III)

wherein Ar and Y have the same meanings as defined above;
n is 0 or an integer of 1 or more, which comprises preparing an aromatic thiol where m is 1 by the process as defined above, and then, oxidizing the resulting compound.

Moreover, the present invention relates to the preparation of an aromatic thiol represented by the formula (I) which comprises allowing (B) an aromatic halogeno compound represented by the formula (IV):

   (IV)

wherein Ar and Y have the same meanings as defined above;
X represents a halogeno group bonded to a carbon atom constituting the aromatic ring of Ar;
m is an integer of 1 or more; and
n is 0 or an integer of 1 or more, to react with (C)(1) a hydrocarbylmercaptide alkali metal salt represented by the formula (V):

   (V)

wherein R has the same meaning as defined above, and M represents an alkali metal;
and/or (C)(2)(a) a hydrocarbyl mercaptane represented by the formula (VI):

   (VI)

wherein R has the same meaning as defined above, and (C)(2)(b) an alkali metal, its hydroxide, carbonate, hydride or alkoxide
in the presence of (D) an aprotic polar solvent to produce an aromatic thioether represented by the formula (II):

   (II)

wherein Y, Ar and R have the same meanings as defined above; and m and n are as defined above;
and the resulting thioether is treated in the same manner as mentioned above.

Also, it relates to a process for the preparation of an aromatic disulfide represented by the formula (III) which comprises producing the aromatic thiol represented by the formula (I) where m is 1 according to the above-mentioned process, and then, subjecting to oxidation.

BEST MODE FOR CARRYING OUT THE INVENTION

In the present specification, the term "aromatic thiol" is used as a concept including, in addition to aromatic monothiol, aromatic compound having a plural number of mercapto groups such as aromatic dithiol, aromatic trithiol, etc., otherwise specifically limited.

The preparation process in the present invention is representatively and particularly preferably applied to the case where Ar is a monovalent or multivalent benzene ring residue such as phenyl, phenylene groups, etc., in the above-mentioned aromatic compounds.

In the following, the present invention will be explained in the order with respect to the process using aromatic halogeno compounds as a starting material. As described above, the preparation process in the present invention includes the second step et seq. by the use of aromatic thioethers obtained by the other process as a starting material. For example, there may be used aromatic thioether obtained by the reaction of an aromatic primary amine with sodium nitrite and an acid, thereby an aromatic diazonium salt is prepared, and then, it is reacted with sodium hydrocarbylmercaptide.

In the present invention, the first step in the preparation of aromatic thiol is the formation of aromatic thioether by the reaction of (B) an aromatic halogeno compound with (C) an organic sulfur compound.

(B) The aromatic halogeno compound to be used in the present invention is a derivative of aromatic ring compound having at least one halogen atom X bonded to the carbon atom of the aromatic ring.

Ar is an aromatic hydrocarbon residue. As Ar, aromatic ring residues such as benzene, biphenyl, terphenyl, naphthalene, anthracene, and pyrene rings are included. In view of the reactivity with (C), benzene residue is particularly preferred.

X is a halogen atom bonded to the carbon atom of the aromatic ring (Ar) and reacts with (C), and may be exemplified by fluoro, chloro, bromo and iodo atoms. Of these, chloro or bromo is preferred since (B) can be easily obtained and the separation of a byproduct(s) is/are easy.

m is an integer of 1 or more, and when Ar is benzene ring, it is an integer of 1 to 6. Where the reaction product is relatively simple, and particularly when products having a disulfide bond are to be obtained by oxidizing aromatic thiol, m is preferably 1.

Y binds to the carbon atom of the aromatic ring Ar and is introduced into the objective aromatic thiol or aromatic disulfide as a substituent(s), and the reaction between (B) and (C) can be promoted due to the presence of Y. Y represents halogeno, nitro, nitrile, sulfone, sulfamoyl or hydrocarbylsulfonyl group. As the halogeno group, there may be mentioned fluoro, chloro, bromo and iodo, and as the hydrocarbylsulfonyl group, there may be exemplified by methyl-sulfonyl, phenylsulfonyl, p-toluylsulfonyl, etc. When a plural number of Ys exist, they may be the same or different from each other. Also, when Y is halogeno, it may be the same as or different from X.

n is 0 or an integer of 1 or more, and when Ar is benzene ring residue, it is 0 or an integer of 1 to 5. When a plural number of Ys are the same, the reaction of (B) and (C) easily proceeds when n is a larger number, and yields of the substituted aromatic thiols are high due to the subsequently carried out elimination reaction. As compared to the other synthetic methods of the aromatic thiols, n is preferably 2 or 3 since the substituted aromatic thiols can be obtained with relatively high yields and purities.

(C) is to introduce a mercapto group(s) to the aromatic ring by the reaction with (B). As (C), the following (1) and/or (2) may be used. That is, (1) is a hydrocarbylmercaptide alkali metal salt having a monovalent hydrocarbyl group with a specific structure in the molecule; and (2) is a combination of (a) hydrocarbyl mercaptane having the similar monovalent hydrocarbyl group and (b) an alkali metal, its hydroxide, carbonate, hydride or alkoxide. The combination of (2) is a precursor substance for forming (1) in the system, and the formed (1) reacts with (B) to obtain aromatic thioethers. Since it can be easily obtained, a combination of (2) is preferably used as (C).

The monovalent hydrocarbyl group R contained in the molecules of (1) and (2)(a) and binds to a sulfur atom can be selected from wide ranges. That is, as R, there may be mentioned a secondary alkyl group having 3 to 20 carbon atoms such as isopropyl, s-butyl, s-pentyl, s-hexyl, s-octyl, s-decyl, s-dodecyl, 1,4,4-trimethylpentyl, etc.; a secondary alkenyl group having 4 to 10 carbon atoms such as isobutenyl, isopentenyl, etc.; a monovalent secondary hydrocarbyl group such as 1-phenylethyl, benzhydryl, etc.; and a monovalent tertiary hydrocarbyl group including a tertiary alkyl group having 4 to 20 carbon atoms such as t-butyl, t-pentyl, t-hexyl, t-octyl, t-decyl, t-dodecyl, 1-methyl-1-ethylpropyl, 1,1-diethylpropyl, 1,1,4-trimethylpentyl, etc.; and an aromatic ring-containing tertiary hydrocarbyl group such as 1-methyl-1-phenylethyl, 1,1-diphenylethyl, trityl, etc.

When a protonic acid is used as (A), the above reaction can be considered to proceed, for example, as follows when t-butyl sulfide is used as the aromatic thioether.

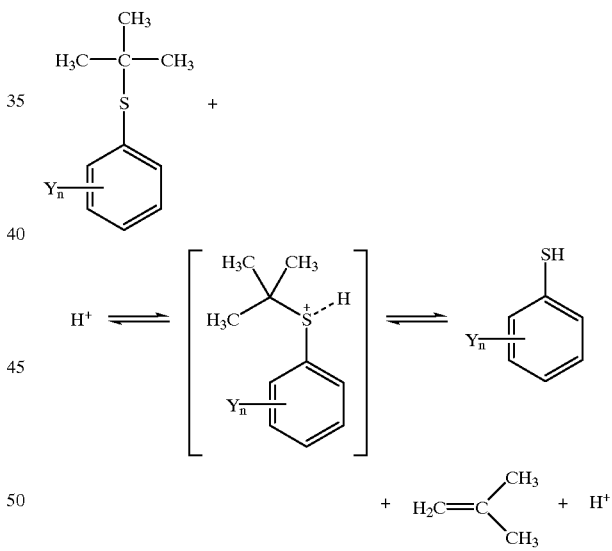

That is, a proton is adducted to the sulfur atom of the aromatic thioether, and then, the substituent R (in the above case, a t-butyl group) of the sulfur atom is eliminated as $R^+$ to form an aromatic thiol, and simultaneously a proton is released from $R^+$ by intramolecular arrangement to form a compound such as an alkene, etc.

Accordingly, when the protonic acid is used, it is required that the monovalent hydrocarbyl groups R contained in (1) and (2) are hydrocarbyl groups capable of being released after formation of a complex with a proton as the aromatic thioether. Such R may include an aliphatic or aromatic monovalent tertiary hydrocarbyl group represented by the formula (VII):

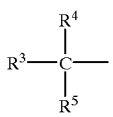

(VII)

wherein $R^3$, $R^4$ and $R^5$ each represent an alkyl group or an aryl group, provided that at least one of $R^3$, $R^4$ and $R^5$ is an aryl group, one of the remaining may be hydrogen; and M represents an alkali metal, or a monovalent diaryl or monoalkylmonoaryl secondary hydrocarbyl group, and further the above-mentioned tertiary alkyl group having 4 to 20 carbon atoms; the above-mentioned aromatic group-containing tertiary hydrocarbyl group; and a secondary aromatic hydrocarbyl group to which two aryl groups are bonded to the carbon atom which binds to the sulfur atom, or each one of an alkyl group and an aryl group is bonded to the same. Among these, a t-butyl group and a benzhydryl group are preferred since synthesis thereof is easy, and the reaction and elimination thereof by an acid are easy. In the formula (VII), M is an alkali metal, and may be mentioned lithium, sodium, potassium, cesium, etc., and sodium and potassium are preferred.

Moreover, when a Lewis acid is used as (A), it can be considered that the above-mentioned reaction proceeds with as follows when toluene is used as a solvent and aluminum chloride is used as a Lewis acid.

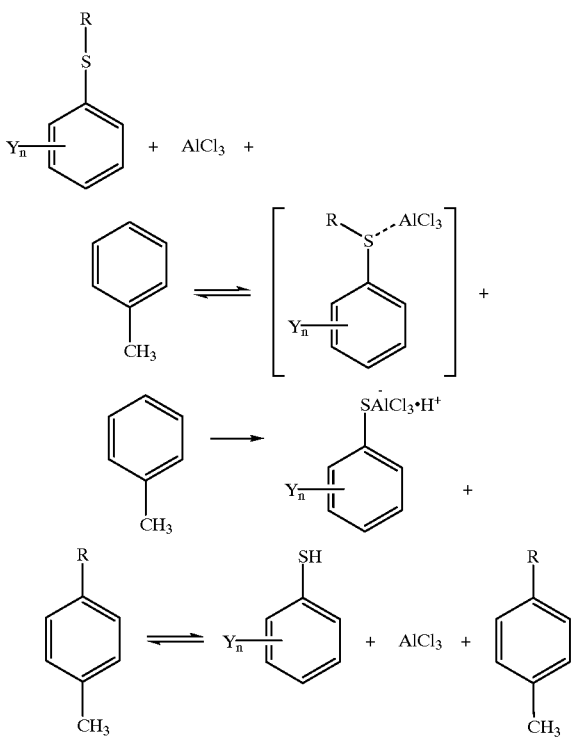

That is, the Lewis acid is coordinated to the sulfur atom of the aromatic thioether, and then, the substituent R at the sulfur atom is eliminated as $R^+$. As mentioned in the above decomposition by the protonic acid, there occurs a reaction in which a proton is released from $R^+$ to form an olefin. However, mainly occurred is a reaction that $R^+$ reacts with a solvent and simultaneously the solvent releases a proton, and the proton is adducted to the aromatic thioether to which the Lewis acid is coordinated and further the Lewis acid is released by intramolecular transition reaction to form an aromatic thiol. Accordingly, in the above-mentioned reaction, it is necessary to exist a solvent which becomes an acceptor of $R^+$.

As the substituent R which can be applied to the above-mentioned reaction, in addition to the substituent of the formula (VII) described in the explanation of the above-mentioned protonic acid, there may be mentioned a specific monovalent hydrocarbyl group represented by the following formula:

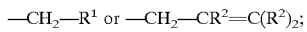

where $R^1$ and $R^2$ have the same meanings as defined above. As $R^1$, there may be exemplified by a monovalent aromatic ring group such as phenyl, 1-naphthyl, etc.; a group in which said aromatic ring group is further substituted by a monovalent hydrocarbyl group (s) such as tolyl, xylyl, 4-biphenylyl, etc. As $R^2$, there may be exemplified by, in addition to hydrogen, an alkyl group having 1 to 6 carbon atoms such as methyl, ethyl, propyl, butyl, etc.; an alkenyl group having 2 to 7 carbon atoms such as vinyl, etc.; and an aryl group such as phenyl, etc. As such monovalent primary hydrocarbyl groups, there may be exemplified by a hydrocarbyl group in which an aromatic group is bonded to a methylene group which is bonded to a sulfur atom such as benzyl, 1-naphthylmethyl, etc.; and a hydrocarbyl group having 2 to 10 carbon atoms in which the hydrocarbyl group between the 2-position and the 3-position of which is an unsaturated bond, such as allyl, 2-buenyl, cinnamyl, propargyl, etc. Among these, isopropyl, t-butyl, benzhydryl and benzyl are preferred, and t-butyl is particularly preferred since (1) or (2)(a) can be easily obtained, handling is easy and the hydrocarbyl group is easily eliminated by the reaction with various kinds of Lewis acids.

M contained in the molecule of (1) or (2)(b) is an alkali metal, and there may be mentioned lithium, sodium, potassium, cesium, etc., and sodium and potassium are preferred.

Such (1) may include secondary hydrocarbylmercaptide sodium salts such as sodium isopropylmercaptide, sodium s-butylmercaptide, sodium s-hexylmercaptide, sodium s-octyl-mercaptide, sodium s-dodecylmercaptide, sodium benzhydryl-mercaptide, etc.; tertiary hydrocarbylmercaptide sodium salts such as sodium t-butylmercaptide, sodium t-pentylmercaptide, sodium t-hexylmercaptide, sodium t-dodecylmercaptide, sodium-1, 1-diphenylethylmercaptide, sodium trytylmercaptide, etc.; primary hydrocarbylmercaptide sodium salts such as sodium allylmercaptide, sodium benzylmercaptide, etc.; and hydromercaptide lithium salts and potassium salts corresponding to these.

(2) is a combination of (a) the hydrocarbylmercaptane having the above-mentioned monovalent hydrocarbyl group, and (b) an alkali metal, its hydroxide, carbonate, hydride or alkoxide. As (2)(a), there may be exemplified by hydrocarbylmercaptanes having a monovalent hydrocarbyl group as exemplified by the above-mentioned (1), and isobutylmercaptane, t-butylmercaptane, benzhydrylmercaptane and benzylmercaptane.

As (2)(b), there may be mentioned, in addition to the above-mentioned alkali metals; alkali metal hydroxides such as lithium hydroxide, sodium hydroxide, potassium hydroxide, etc.; alkali metal carbonates such as lithium carbonate, sodium carbonate, potassium carbonate, etc.; alkali metal hydrides such as sodium hydride, lithium hydride, etc.; and sodium alkoxides such as sodium methoxide, sodium ethoxide, sodium propoxide (including its isomer), sodium butoxide (including its isomers), etc.; and lithium alkoxides and potassium alkoxides corresponding thereto.

With regard to amounts of (a) and (b) to be used, if one of which is used in excess amount, the reaction may proceed, but it is preferably used in an amount of, as a molar ratio of (b) to (a), 1.0 to 1.5, more preferably 1.0 to 1.1, most preferably 1.0. However, if it is not preferred to remain (a), (b) may be used in a slightly excessive amount.

An amount of (C) to be applied to the reaction with (B) is, when (C) is used in combination with (2), for example, when m=1, generally in the range of 1 to 3 mol, preferably 1.0 to 1.1 mol, and most preferably 1.0 mol to avoid complexity to remove (C) after the reaction, based on 1 mol of (B) in terms of the theoretical amount of (1) formed in the system.

The aprotic polar solvent (D) to be used in the present invention is a reaction solvent which remarkably promote the reaction of the aromatic thiol according to the reaction of (B) and (C). As (D), there may be exemplified by N-methyl-2-pyrrolidone, N,N-dimethylformamide, N,N-dimethylacetamide, sulforane, dimethylsulfoxide, etc., and dimethylsulfoxide is preferred since it is excellent in a reaction promoting effect. (D) is used in an amount necessary to dissolve or disperse the compounds participating in the reaction and to make the system capable of stirring. More specifically, it is generally 200 g or more, preferably in the range of 400 to 1,200 g based on 1 mol of the total amount of (B) and (C).

The step of synthesizing aromatic thioether from (B) an aromatic halide and (C) a sulfur compound is carried out in the presence of the above-mentioned (D) aprotic polar solvent. For example, when (1) hydrocarbylmercaptide alkali metal salt is used as (C), said (1) and (B) are dissolved in the above-mentioned (D). When (2), i.e., (a) and (b) are used as (C), (a) and (b) are dissolved in (D) and heated at 35 to 60° C., the reaction rapidly proceeds to form (1) so that it is then reacted with (B) in the same manner as mentioned above.

The reaction of (B) and (C) can be carried out at a room temperature to 200° C. When the sum of n and m of (B) is relatively little as 2 to 4, it is effective to promote the reaction preferably by heating the mixture at 50 to 120° C. When m is 2 or more, it is preferred to effect the reaction at 100 to 200° C. Incidentally, when Y is an electron attractive group such as a nitro group, and when Ar is a benzene ring and the sum of n and m is 5 or 6, the reaction sufficiently proceeds at a room temperature so that a room temperature is preferred.

The second step in the production process of the aromatic thiol is, when a Lewis acid is used as (A), a step for the preparation of aromatic thiol by reacting the aromatic thioether in which a monovalent hydrocarbyl group having a specific structure as mentioned above obtained in the first step with a Lewis acid, and then subjecting to hydrolysis to eliminate the hydrocarbyl group from said aromatic compound.

In the present invention, (A) the Lewis acid can be defined as a concept including its complex. As (A) the Lewis acid, there may be exemplified by halides such as boron trifluoride, boron trichloride, boron tribromide, aluminum chloride, aluminum bromide, titanium tetrachloride, ferric chloride, tin tetrachloride, antimony pentoxide, etc.; and complexes thereof such as boron trifluoride-diethyl ether complex; and preferred are boron bromide, aluminum chloride, titanium tetrachloride and ferric chloride since they can be easily handled and their activities are high. Also, to obtain the aromatic thiol with high purity, those having no oxidative power are more preferably used, and aluminum chloride and titanium tetrachloride are particularly preferred.

An amount of (A) the Lewis acid to be used may vary depending on the kind of the aromatic thioether, i.e., Y, R, m and n, as well as the kind of the Lewis acid, but may be optionally selected from a catalytic amount to an excess amount to the aromatic thioether. That is, an amount of the Lewis acid is generally 0.01 to 3 mol, preferably in the range of 0.02 to 1.1 mol based on 1 mol of the aromatic thioether to be applied to the reaction in view of providing a suitable elimination reaction rate to the various kinds of hydrocarbyl groups to be eliminated from the aromatic thioether and causing no unpleasant side reaction. The reaction proceeds in the presence of a minor amount of the Lewis acid when n is larger number and m is smaller number. The Lewis acid is more preferably used in a catalytic amount of 0.02 to 0.1 mol based on the above-mentioned standard in view of economical merits and easiness in removal of the remaining acid.

The catalytic reaction of the aromatic thioether and the Lewis acid can be carried out by optionally selecting the temperature from less than a room temperature to up to 200° C., and preferably at a room temperature to 150° C. depending on the strength of these acids. As the solvent to be used in the reaction, there may be used aromatic hydrocarbons such as toluene, xylene, mesitylene, etc.; aromatic ethers such as anisole, etc.; halogenated hydrocarbons such as methylene chloride, chloroform, carbon tetrachloride, ethylene dichloride, etc. When the halogenated hydrocarbon is used, the reaction is preferably carried out in the presence of aromatic hydrocarbon such as toluene, xylene, mesitylene, etc.; or aromatic ether such as anisole which are an acceptor of $R^+$. When boron trifluoride, boron tribromide, aluminum chloride, titanium tetrachloride, ferric chloride, etc. are used as the Lewis acid, the reaction is preferably carried out in the presence of the above-mentioned solvent at a room temperature.

Then, water is added to the reaction mixture whereby said reaction product is hydrolyzed to form aromatic thiol. The hydrolysis proceeds within a short period of time, but when the reaction is exothermic, it is preferred to use an excessive amount of cold water and/or ice.

On the other hand, when the protonic acid is used as (A), the second step of the preparation of the aromatic thiol is a step in which aromatic thiol is prepared by the reaction of the aromatic thioether which has a specific monovalent hydrocarbyl group bonded to the sulfur atom as mentioned above obtained in the first step with a protonic acid thereby the hydrocarbyl group is eliminated from said aromatic compound.

As (A) the protonic acid, there may be exemplified by hydrohalonenated acids such as hydrofluoric acid, hydrochloric acid, hydrobromic acid, etc.; hydrogen bromide-acetic acid; sulfuric acid; sulfonic acids such as benzenesulfonic acid, p-toluenesulfonic acid, methanesulfonic acid, etc., and p-toluenesulfonic acid and methanesulfonic acid are preferred since their catalytic activities are high, they are non-volatile and suitable for a heating reaction and are capable of effecting elimination of the hydrocarbyl group effectively. These protonic acids may be applied to the reaction in the form of a hydrate, but in this case, the reaction becomes markedly slow so that it is preferred to use them after dehydration. It is also preferred for the reaction to use the protonic acid dissolved in aliphatic acid such as acetic acid in place of water.

(A) The protonic acid is generally used in an amount within the range of 0.1 to 5 mol, preferably 0.2 to 3 mol, particularly preferably 1.0 mol based on 1 mol of the aromatic thioether to be applied to the reaction since a suitable rate of the elimination reaction can be obtained with respect to various kinds of hydrocarbyl groups and no unpleasant side reaction occurs.

The reaction between the aromatic thioether and the protonic acid is generally carried out at 100 to 200° C. to promote the reaction, more preferably 100 to 150° C. to reduce side reactions. To make control of the reaction temperature easy and to absorb hydrocarbons such as isobutylene, etc. formed by the elimination reaction as shown in the reaction formula with regard to the reaction mechanism of the above-mentioned protonic acid, the reaction is preferably carried our under reflux of a solvent having a boiling point at the reaction temperature region including hydrocarbons such as toluene, xylene, mesitylene, etc.; ethers such as anisole, etc. Also, in particular, the reaction can proceed by the use of a solvent which can azeotrope with water such as toluene, anisole, etc. and addition of the protonic acid to the reaction system as a hydrate or in the presence of water while dehydrating.

Thus, synthesis of the aromatic thioether and the elimination reaction of the hydrocarbyl group of said thioether are carried out in combination, aromatic thiol can be synthesized with good yield and high purity.

The aromatic thiol thus obtained may be used as an intermediate for synthesizing various kinds of compounds, or may be used to produce aromatic disulfide by dimerizing the aromatic thiol where m=1 by oxidation, as the third step.

Said oxidation reaction can be carried out by addition an oxidizing agent with stirring. Bromine, iodine, hydrogen peroxide, sulfuric acid, peracetic acid, ferric chloride, antimony pentoxide, tin tetrachloride, etc. may be used as the oxidizing agent. Among these, iodine or hydrogen peroxide is preferred since the reaction can be easily carried out with good yield. Also, oxidation reaction may be carried out by introducing air or oxygen. The reaction proceeds at a room temperature, and may be carried out under heating or cooling, if necessary. Moreover, the above-mentioned reaction may be carried out after dissolution of the aromatic thiol in organic solvents such as toluene, xylene, etc. to promote the reaction smoothly.

The Lewis acid such as ferric chloride, tin tetrachloride, antimony pentoxide and the protonic acid such as sulfuric acid can be used as a reactant to synthesize aromatic thiol from aromatic thioether. Therefore, the synthesis of aromatic thiol where m is 1 from aromatic thioether and synthesis of aromatic disulfide can be carried out with one step without isolating the aromatic thiol by the use of a Lewis acid or a protonic acid having the above-mentioned reactivity and function of oxidation under suitable reaction conditions. As the Lewis acid for the one-step synthesis of aromatic disulfide from aromatic thioether, ferric chloride is preferred since it has high power. Also, when the elimination reaction is carried out by the use of 95% conc. sulfuric acid under reflux of toluene, both of aromatic thiol and disulfide can be prepared. To the contrary, when the reaction proceeds with dehydration by azeotropic distillation in toluene, aromatic disulfides can be produced with high yield of 70% or more based on the theoretical amount without isolation of aromatic thiol.

Utilizability in Industry

According to the present invention, aromatic thiol and aromatic disulfide can be obtained from aromatic thioether having a substituent(s) on the aromatic ring with excellent yield and high purity.

In the present invention, the reaction proceeds with a catalytic amount of a Lewis acid, which could not be expected in a Friedel-Crafts reaction using a Lewis acid. This makes removal of the remaining acid easy and is industrially extremely advantageous.

Also, according to the above findings, aromatic thiol and aromatic disulfide can be produced from aromatic halogenated compound having a substituent(s) through aromatic thioether with high yield and purity. The processes of the present invention are particularly useful for production of di-substituted aromatic thiol and disulfide which can not be obtained with high yield by the other processes.

The aromatic thiols and the aromatic disulfides obtained by the present invention are useful intermediates for medicines, agricultural chemicals, electronic materials, etc.

EXAMPLES

In the following, the present invention will be described in more detail by referring to Examples. In Examples, "part" means "part by weight" and "%" in the composition means "% by weight". In the following reaction formula, i-Pr means an isopropyl group, t-Bu means a t-butyl group, Bzl means a benzyl group, Ph means a phenyl group, and DMSO means dimethylsulfoxide. Incidentally, the present invention is not limited by these Examples.

Example 1

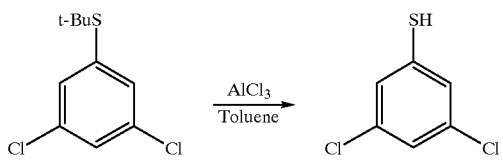

In a reaction vessel equipped with a stirrer, a calcium chloride tube, a thermometer and a dropping funnel were charged, under nitrogen atmosphere, 14.7 parts of aluminum chloride and 100 parts of toluene, and under ice-cooling, 23.5 parts of 3,5-dichlorophenyl-t-butylsulfide were added dropwise to the mixture. After stirring at room temperature for 30 minutes, the reaction mixture was poured into 150 parts of ice and, after vigorously stirring, the mixture was allowed to stand and the liquids were separated. To the organic phase were added 200 parts of a 10% aqueous sodium hydroxide solution, and after stirring the mixture, it was allowed to stand and the liquids were separated. To the aqueous phase was added 12 N hydrochloric acid to adjust the pH 2, crystals were precipitated. This crystals were separated by filtration to obtain 16.6 parts of colorless needle crystals.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 93% based on the theoretical amount.

Example 2

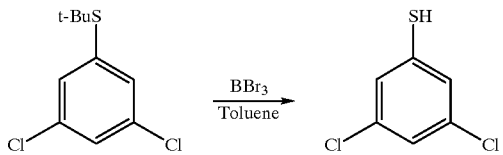

In the same manner as that in Example 1 except for using 27.6 parts of boron bromide in place of aluminum chloride, the procedure was carried out and 15.2 parts of colorless needle crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 85% based on the theoretical amount.

Example 3

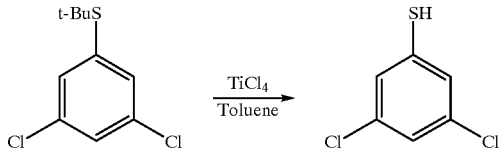

In the same manner as that in Example 1 except for using 20.9 parts of titanium tetrachloride in place of aluminum chloride, at room temperature for 8 hours, the procedure was carried out and 16.9 parts of colorless needle crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 95% based on the theoretical amount.

Example 4

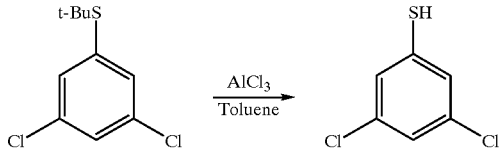

In the same manner as that in Example 1 except for changing an amount of aluminum chloride (0.27 part) and an amount of toluene (50 parts), at room temperature for 2 hours, the procedure was carried out and 17.2 parts of colorless needle crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 96% based on the theoretical amount.

Example 5

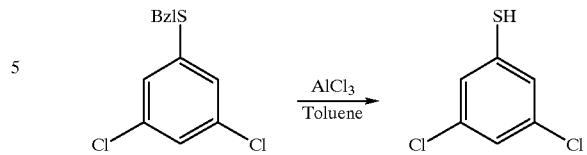

In the same manner as that in Example 1 except for using 26.9 parts of 3,5-dichlorophenylbenzylsulfide in place of 3,5-dichlorophenyl-t-butylsulfide, at room temperature for 3 hours, the procedure was carried out and 16.3 parts of colorless needle crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 91% based on the theoretical amount.

Example 6

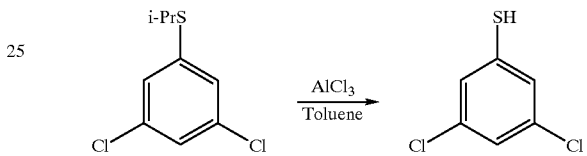

In the same manner as that in Example 1 except for using 22.1 parts of 3,5-dichlorophenylisopropylsulfide in place of 3,5-dichlorophenyl-t-butylsulfide, under reflux by heating for one hour after completion of the dropwise addition, the procedure was carried out and 15.7 parts of colorless needle crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 88% based on the theoretical amount.

Example 7

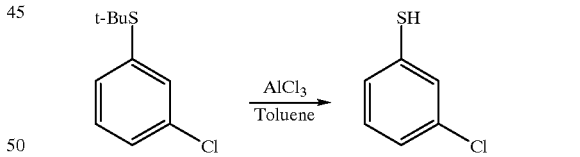

In the same manner as that in Example 1 except for using 20.1 parts of 3-chlorophenyl-t-butylsulfide in place of 3,5-dichlorophenyl-t-butylsulfide, at room temperature for 5 hours, the procedure was carried out up to adjusting a pH of the aqueous phase to 2, then oily product was precipitated. After extracting the product with diethyl ether, the solvent was removed under reduced pressure and the residue was distilled under reduced pressure, and 8.8 parts of colorless transparent liquid were obtained as a fraction having a boiling point of 110° C./30 Torr.

$^1$H-NMR (CDCl$_3$): δ7.25 (m, 1H), 7.12 (m, 3H), 3.48 (s, 1H).

As the result, the product was confirmed to be 3-chlorothiophenol. The yield was 61% based on the theoretical amount.

Example 8

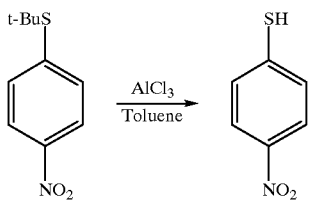

In the same manner as that in Example 1 except for using 21.1 parts of 4-nitrophenyl-t-butylsulfide in place of 3,5-dichlorophenyl-t-butylsulfide, the procedure was carried out and 13.5 parts of pale yellowish needle crystals were obtained.

Melting point: 77° C.;
$^1$H-NMR (CDCl$_3$): δ8.09 (d, J=8.9 Hz, 2H), 7.36 (d, J=8.9 Hz, 2H), 3.80 (s, 1H).

As the result, the product was confirmed to be 4-nitrothiophenol. The yield was 87% based on the theoretical amount.

Example 9

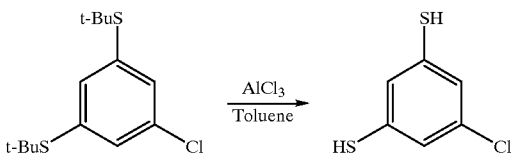

In the same manner as that in Example 1 except for using 28.8 parts of 3,5-bis(t-butylthio)chlorobenzene in place of 3,5-dichlorophenyl-t-butylsulfide, changing the amount of aluminum chloride (14.7 parts), at room temperature for 8 hours, and changing the amount of a 10% aqueous sodium hydroxide to be added at the post-treatment (400 parts), the procedure was carried out and 15.0 parts of colorless needle crystals were obtained.

Melting point: 55° C.;
$^1$H-NMR (CDCl$_3$): δ7.03 (s, 3H), 3.47 (s, 2H).

As the result, the product was confirmed to be 5-chloro-1,3-benzenedithio. The yield was 85% based on the theoretical amount.

Example 10

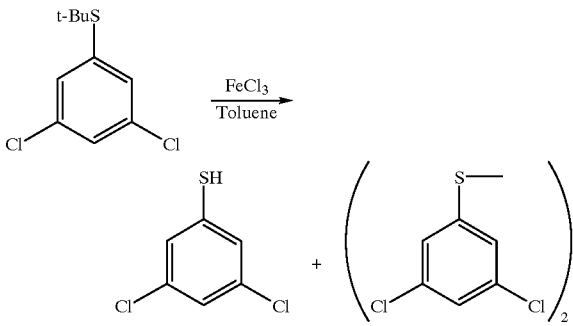

In the same reaction vessel used in Example 1 were charged 17.8 parts of ferric chloride and 100 parts of toluene under nitrogen atmosphere, and then, 23.5 parts of 3,5-dichlorophenyl-t-butylsulfide were added dropwise under ice-cooling. After stirring the mixture at room temperature for 30 minutes, the reaction mixture was poured into 150 parts of ice and after vigorously stirring the mixture, it was allowed to stand to separate the liquids. To the organic phase were added 200 parts of a 10% aqueous sodium hydroxide solution, the mixture was stirred and again allowed to stand. The liquids were separated and the organic phase was collected, washed with a saturated saline solution and dehydrated over anhydrous sodium sulfate. Thereafter, toluene was removed by distillation under reduced pressure and a pale yellowish liquid was obtained. This liquid was treated by methanol and 13.3 parts of white crystals were obtained.

Melting point: 65° C.;
$^1$H-NMR (CDCl$_3$): δ7.33 (d, J=1.7 Hz, 4H), 7.23 (t, J=1.7 Hz, 2H)

As the result, the product from the organic phase was confirmed to be bis(3,5-dichlorophenyl)disulfide. The yield was 75% based on the theoretical amount.

To the combined aqueous phases was added a 12N aqueous hydrochloric acid solution to adjust the pH of the mixture to 2, and the precipitated crystals were collected by filtration and 1.3 parts of colorless needle crystals were obtained.

Melting point: 62° C.;
$^1$H-NMR (CDCl$_3$): δ7.15 (s, 3H), 3.55 (s, 1H).

As the result, the product from the aqueous phase was confirmed to be 3,5-dichlorothiophenol. The yield was 7% based on the theoretical amount.

Example 11

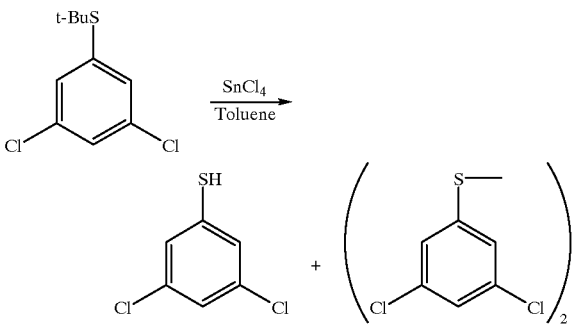

In the same manner as that in Example 1 except for using 28.7 parts of tin tetrachloride in place of ferric chloride and carrying out the reaction by heating the system after completion of addition of 3,5-dichlorophenyl-t-butylsulfide and refluxing toluene for 56 hours, the procedure was carried out and 7.0 parts of white crystals were obtained.

Melting point: 65° C.;
$^1$H-NMR (CDCl$_3$): δ7.33 (d, J=1.7 Hz, 4H), 7.23 (t, J=1.7 Hz, 2H).

As the result, the product from the organic phase was confirmed to be bis(3,5-dichlorophenyl)disulfide. The yield was 39% based on the theoretical amount.

Also, similarly, 6.3 parts of colorless needle crystals were obtained from the aqueous phase.

Melting point: 62° C.;
$^1$H-NMR (CDCl$_3$): δ7.15 (s, 3H), 3.55 (s, 1H).

As the result, the product from the aqueous phase was confirmed to be 3,5-dichlorothiophenol. The yield was 35% based on the theoretical amount.

Example 12

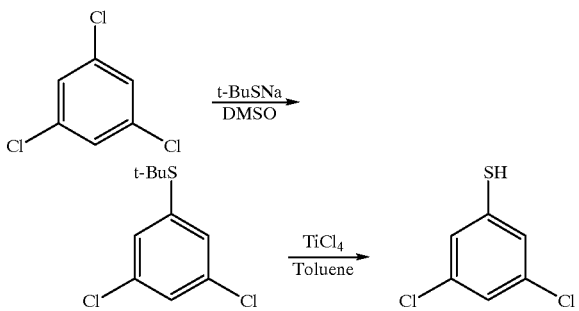

First Step

In a reaction vessel equipped with a stirrer, a Dimroth condenser, a thermometer and a dropping funnel were charged, under nitrogen atmosphere, 22.4 parts of sodium t-butyl-mercaptide, 200 parts of dimethylsulfoxide and 36.3 parts of 1,3,5-trichlorobenzene, and the temperature of the mixture was slowly raised while stirring, and heated at 80° C. for 5 hours. Then, the mixture was cooled to room temperature, 200 parts of water and 200 parts of toluene were added thereto, and then, the mixture was allowed to stand and the liquids were separated. The organic phase was washed with a saturated saline solution, dehydrated over anhydrous sodium sulfate, and then, toluene was removed by distillation under reduced pressure. According to distillation under reduced pressure of the liquid residue, 37.8 parts of colorless transparent liquid was obtained as a fraction of a boiling point of 75° C./0.4 Torr.

$^1$H-NMR (CDCl$_3$): δ7.42 (d, J=2.0 Hz, 2H), 7.36 (d, J=2.0 Hz, 1H), 1.31 (s, 9H).

As the result, the product was confirmed to be 3,5-dichlorophenyl-t-butylsulfide. The yield was 80% based on the theoretical amount.

Second Step

In the same manner as that in Example 3 except for using the thus obtained 3.5 parts of 3,5-dichlorophenyl-t-butylsulfide and 20.9 parts of titanium tetrachloride, the procedure was carried out and 16.9 parts of colorless needle crystals were obtained.

Melting point: 62° C.;

$^1$H-NMR (CDCl$_3$): δ7.15 (s, 3H), 3.55 (s, 1H).

As the result, the product from the aqueous phase was confirmed to be 3,5-dichlorothiophenol. The yield was 95% based on the theoretical amount.

Example 13

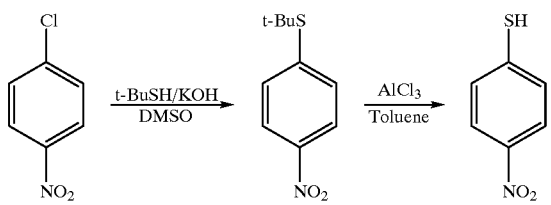

First Step

In the reaction vessel used in the first step of Example 12 were charged, under nitrogen atmosphere, 18.0 parts of t-butylmercaptane, 200 parts of dimethylsulfoxide and 14.5 parts of 85% potassium hydroxide, and the mixture was stirred at 50° C. for 30 minutes whereby potassium t-butylmercaptide was synthesized in the system. Subsequently, 31.6 parts of p-nitrochlorobenzene were added to the mixture under ice-cooling, and the resulting mixture was stirred at room temperature for 30 minutes. Then, In the same manner as that in the first step of Example 12 after addition of water and toluene, the procedure was carried out and 36.8 parts of colorless liquid with a boiling point of 99° C./0.5 Torr were obtained.

$^1$H-NMR (CDCl$_3$): δ8.17 (d, J=8.9 Hz, 2H), 7.68 (d, J=8.9 Hz, 2H), 1.35 (s, 9H).

As the result, the product was confirmed to be 4-nitrophenyl-t-butylsulfide. The yield was 87% based on the theoretical amount.

Second Step

In the same manner as that in Example 8 except for using the thus obtained 21.1 parts of 4-nitrophenyl-t-butylsulfide and 14.7 parts of aluminum chloride, the procedure was carried out and 13.5 parts of pale yellowish needle crystals were obtained.

Melting point: 77° C.;

$^1$H-NMR (CDCl$_3$): δ8.09 (d, J=8.9 Hz, 2H), 7.36 (d, J=8.9 Hz, 2H), 3.80 (s, 1H).

As the result, the product was confirmed to be 4-nitrothiophenol. The yield was 87% based on the theoretical amount.

Example 14

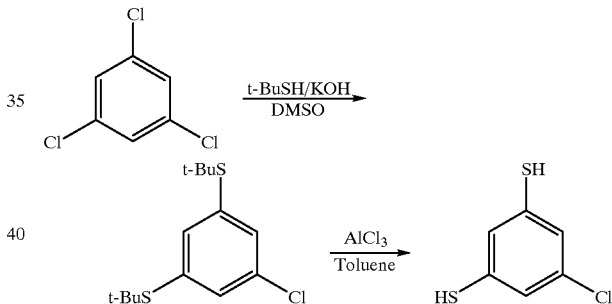

First Step

In the same manner as that in the first step of Example 13 except for changing the added amount of t-butylmercaptane to 36.0 parts, changing the added amount of 85% potassium hydroxide to 29 parts, adding 36.3 parts of 1,3,5-trichlorobenzene in place of p-nitrochlorobenzene, and heating at 130° C. for 3 hours, the procedure was carried out up to removal of toluene to obtain pale yellowish crystal state residue. This material was recrystallized from methanol and 45.8 parts of colorless platy crystals were obtained.

Melting point: 89° C.;

$^1$H-NMR (CDCl$_3$): δ7.61 (t, J=1.6 Hz, 1H), 7.53 (d, J=1.6 Hz, 2H), 1.30 (s, 18H).

As the result, the product was confirmed to be 3,5-bis(t-butylthio) chlorobenzene. The yield was 79% based on the theoretical amount.

Second Step

In the same manner as that in Example 9 except for using the thus obtained 28.8 parts of 3,5-bis(t-butylthio) chlorobenzene and 14.7 parts of aluminum chloride, the procedure was carried out and 15.0 parts of colorless needle crystals were obtained.

Melting point: 55° C.;
$^1$H-NMR (CDCl$_3$): δ7.03 (s, 3H), 3.47 (s, 2H).

As the result, the product was confirmed to be 5-chloro-1,3-benzenedithiol. The yield was 85% based on the theoretical amount.

Example 15

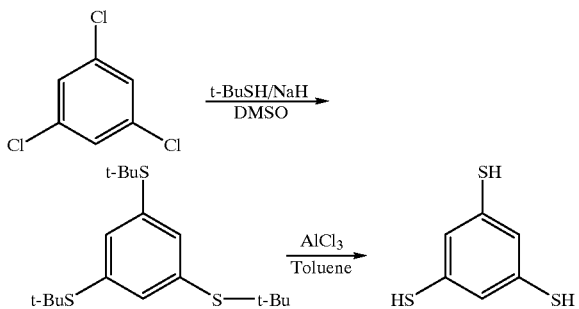

First Step

In a reaction vessel equipped with the same attachment devices used in Example 12, the first step were charged, under nitrogen atmosphere, 300 parts of dimethylsulfoxide and 34.2 parts of sodium hydride with a concentration of 63.2% dispersed in a mineral oil, and the mixture was stirred at room temperature for 30 minutes. Next, 81.2 parts of t-butylmercaptane was slowly added dropwise to the mixture, and then, 36.2 parts of 1,3,5-trichlorobenzene was added to the resulting mixture and the temperature of the resulting mixture was slowly raised and heated at 150° C. for 2 hours. Then, the mixture was cooled to room temperature, 400 parts of water and 200 parts of toluene were added thereto, and the resulting mixture was stirred. Then, the mixture was allowed to stand and the liquids were separated. The organic phase collected was washed successively with a 10% aqueous sodium hydroxide solution, and a saturated saline solution, dehydrated over anhydrous sodium sulfate, and then, toluene was removed by distillation under reduced pressure. The residue was recrystallized from isopropyl alcohol and 41.0 parts of colorless platy crystals were obtained.

Melting point: 132 to 133° C.;
$^1$H-NMR (CDCl$_3$): δ7.24 (s, 3H), 1.30 (s, 27H).

As the result, the product was confirmed to be 1,3,5-tris(t-butylthio)benzene. The yield was 60% based on the theoretical amount.

Second Step

In the reaction vessel used in Example 1 were charged, under nitrogen atmosphere, 4.0 parts of aluminum chloride and 500 parts of toluene, and under ice-cooling, 34.3 parts of 1,3,5-tris(t-butylthio)benzene obtained in the first step was added dropwise to the mixture. After the mixture was stirred at room temperature for 5 hours, the reaction product was poured into 150 parts of ice, and the resulting mixture was vigorously stirred. After allowing to stand, the liquids were separated to collect the organic phase, and to the organic phase were added 600 parts of a 10% aqueous sodium hydroxide solution and the resulting mixture was stirred. After allowing to stand, the liquids were separated to collect the aqueous phase, and when the pH of the aqueous phase was adjusted to 2 by addition of hydrochloric acid, crystals were precipitated. These crystals were collected by filtration and 16.9 parts of colorless needle crystals were obtained.

Melting point: 56 to 59° C.;
$^1$H-NMR (CDCl$_3$): δ6.94 (s, 3H), 3.41 (s, 3H).

As the result, the product was confirmed to be 1,3,5-trimercaptobenzene. The yield was 97% based on the theoretical amount.

Example 16

First Step

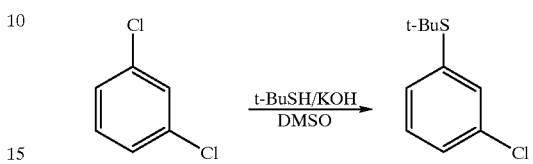

In a reaction vessel equipped with a stirrer, a Dimroth condenser, a thermometer and a dropping funnel were charged, under nitrogen atmosphere, 18.0 parts of t-butylmercaptane, 200 parts of dimethylsulfoxide and 15.4 parts of 85% potassium hydroxide, and the mixture was stirred at 50° C. for 30 minutes so that potassium t-butylmercaptide was synthesized in the system. Subsequently, 29.4 parts of 1,3-dichlorobenzene were added to the mixture, and the temperature of the mixture was slowly raised while stirring, and heated at 120° C. for 7 hours. Then, the mixture was cooled to room temperature, and after adding 200 parts of water and 200 parts of toluene and stirring the mixture, the mixture was allowed to stand and the liquids were separated. The organic phase was washed with a saturated saline solution, dehydrated over anhydrous sodium sulfate, and then, toluene was removed by distillation under reduced pressure. According to distillation of the liquid residue under reduced pressure, 33.0 parts of colorless transparent liquid with a fraction having a boiling point of 142° C./32 Torr were obtained.

$^1$H-NMR (CDCl$_3$): δ7.54 (dd, J=1.7, 2.0 Hz, 1H), 7.41 (ddd, J=1.3, 2.0, 7.7 Hz, 1H), 7.34 (ddd, J=1.3, 1.7, 7.6 Hz, 1H), 7.25 (t, J=6.7 Hz, 1H), 1.29 (S, 9H).

As the result, the product was confirmed to be 3-chlorophenyl-t-butylsulfide. The yield was 82% based on the theoretical amount.

Second Step

In a reaction vessel equipped with a stirrer, a Dimroth condenser, a thermometer and a Dean-Stark capturing apparatus were charged, under nitrogen atmosphere, 20.1 parts of 3-chlorophenyl-t-butylsulfide, 19.0 parts of p-toluenesulfonic acid monohydrate and 100 parts of toluene, and the mixture was refluxed under heating for 5 hours while removing water. The mixture was cooled to room temperature, and after adding 150 parts of water and stirring the mixture, it was allowed to stand and the liquids were separated. To the organic phase was added 200 parts of a 10% aqueous sodium hydroxide solution and the mixture was stirred, then it was allowed to stand and the liquids were separated. When 12N aqueous hydrochloric acid solution was added to the aqueous phase thereby the pH was adjusted to 2, and an oily product was precipitated at the bottom portion. The precipitated oily product was extracted by adding 100 parts of toluene. The resulting organic phase was washed with a saturated saline solution, and dehydrated over anhydrous sodium sulfate. Toluene was removed by distillation under reduced pressure, and 9.5 parts of colorless transparent liquid with a fraction having a boiling point of 110° C./30 Torr were obtained according to distillation under reduced pressure.

$^1$H-NMR (CDCl$_3$): δ7.25 (m, 2H), 7.12 (m, 3H), 3.48 (S, 1H).

As the result, the product was confirmed to be 3-chlorothiophenol. The yield was 65% based on the theoretical amount.

Example 17

First Step

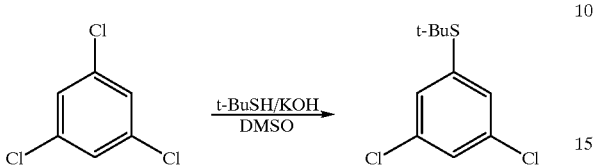

In the same manner as that in the first step of Example 16 except for using 36.3 parts of 1,3,5-trichlorobenzene in place of 1,3-dichlorobenzene at 80° C. for 5 hours, the procedure was carried out and 37.8 parts of a colorless liquid with a boiling point of 75° C./0.4 Torr were obtained.

$^1$H-NMR (CDCl$_3$): δ7.42 (d, J=2.0 Hz, 2H), 7.36 (d, J=2.0 Hz, 1H), 1.31 (s, 9H).

As the result, the product was confirmed to be 3,5-dichlorophenyl-t-butylsulfide. The yield was 80% based on the theoretical amount.

Second Step

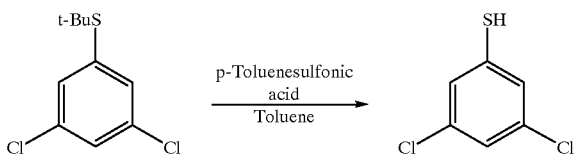

In the same manner as that in the second step of Example 16, except for using 23.5 parts of 3,5-dichlorophenyl-t-butylsulfide in place of 3-chlorophenyl-t-butylsulfide for the refluxing time of 3 hours, the procedure was carried out, and a pH was adjusted to 2 so that crystals were precipitated. This precipitates were collected by filtration and 13.3 parts of colorless needle crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 74% based on the theoretical amount.

Example 18

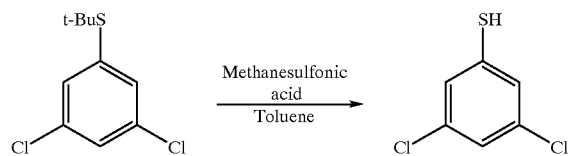

The same manner as that in the first step of Example 17 was carried out and 3,5-dichlorophenyl-5-butylsulfide was obtained. In the reaction vessel used in the second step of Example 16 were charged, under nitrogen gas atmosphere, 23.5 parts of said 3,5-dichlorophenyl-t-butylsulfide, 100 parts of xylene and 1.9 parts of methanesulfonic acid, and the mixture was refluxed under heating for 10 hours while removing isobutylene formed by passing a nitrogen gas thereinto. According to the same procedure as that in the second step of Example 17, 12.4 parts of colorless needle crystals were obtained.

Melting point: 62° C.;

$^1$H-NMR (CDCl$_3$): δ7.15 (s, 3H), 3.55 (s, 1H)

As the result, the product was confirmed to be 3,5-dichlorothiophenol. The yield was 69% based on the theoretical amount.

Example 19

First Step

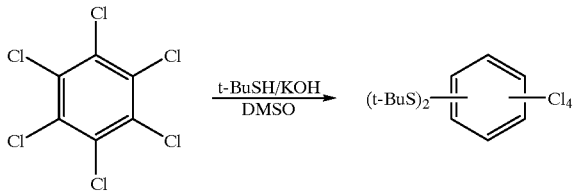

In the same manner as that in the first step of Example 16 except for changing the amount of t-butylmercaptane to be added to 36.1 parts, changing the amount of 85% potassium hydroxide to be added (29 parts), using 57.0 parts of hexachlorobenzene in place of 1,3-dichlorobenzene and subjecting to stirring at room temperature without heating overnight, the procedure was carried out up to removal of toluene, then, a pale yellowish crystalline residue was obtained. This was recrystallized from isopropanol and 64.5 parts of colorless needle crystals were obtained.

Melting point: 142° C.;

Elemental Analysis value as C$_{14}$H$_{18}$Cl$_4$S$_2$, calculated value C, 42.87%; H; 4.63%; measured value C; 42.64%; H: 4.27%.

$^1$H-NMR (CDCl$_3$): δ1.42 (s, 18H).

As the result, the product was confirmed to be bis(t-butylthio) tetrachlorobenzene. The yield was 83% based on the theoretical amount.

Second Step

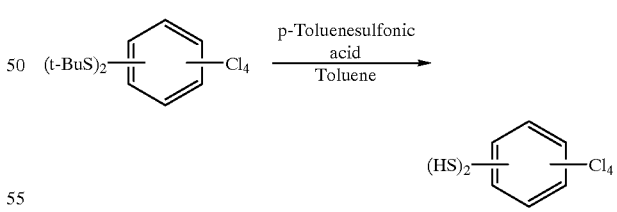

In the same manner as that in the second step of Example 16, except for using 39.2 parts of bis(t-butylthio) tetrachlorobenzene obtained in the first step in place of 3-chlorophenyl-t-butylsulfide, for the refluxing time of 1 hour and changing the amount of a 10% aqueous sodium hydroxide solution to be added after separating liquids (400 parts), the procedure was carried out, and a pH was adjusted to 2 so that crystals were precipitated. This precipitates were collected by filtration and 26.0 parts of white crystals were obtained.

Melting point: 260° C.;

$^1$H-NMR (CDCl$_3$): δ4.86 (s, 2H).

As the result, the product was confirmed to be tetrachlorobenzenedithiol. The yield was 93% based on the theoretical amount.

Example 20

First Step

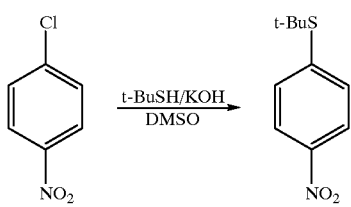

In the same manner as that in the first step of Example 16 except for using 31.6 parts of p-nitrochlorobenzene under ice-cooling in place of 1,3-dichlorobenzene and subjecting to stirring at room temperature for 30 minutes, the procedure was carried out and 36.8 parts of a colorless liquid with a boiling point of 99° C./0.5 Torr was obtained.

$^1$H-NMR (CDCl$_3$): δ8.17 (d, J=8.9 Hz, 2H), 7.68 (d, J=8.9 Hz, 2H) 1.35 (s, 9H).

As the result, the product was confirmed to be 4-nitrophenyl-t-butylsulfide. The yield was 87% based on the theoretical amount.

Second Step

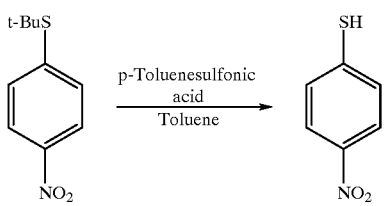

In the same manner as that in the second step of Example 16 except for adding 21.1 parts of 4-nitrophenyl-t-butylsulfide obtained in the first step in place of 3-chlorophenyl-t-butylsulfide under the reflux of 4 hours, the procedure was carried out, and a pH was adjusted to 2 so that crystals were precipitated. This precipitates were collected by filtration and 11.2 parts of pale yellowish crystals were obtained.

Melting point: 77° C.;

$^1$H-NMR (CDCl$_3$): δ8.09 (d, J=8.9 Hz, 2H), 7.36 (d, J=8.9 Hz, 2H), 3.80 (s, 1H).

As the result, the product was confirmed to be 4-nitrothiophenol. The yield was 72% based on the theoretical amount.

Example 21

First Step

In the same manner as that in the first step of Example 17 except for changing the amount of t-butylmercaptane to be added (36.0 parts), changing the amount of 85% potassium hydroxide to be added (29 parts), and heating at 130° C. for 3 hours after the addition, the procedure was carried out up to removal of toluene, then, a pale yellowish crystalline residue was obtained. This was recrystallized from methanol and 45.8 parts of colorless platy crystals was obtained.

Melting point: 89° C.;

$^1$H-NMR (CDCl$_3$): δ7.61 (t, J=1.6 Hz, 1H), 7.53 (d, J=1.6 Hz, 2H), 1.30 (s, 18H).

As the result, the product was confirmed to be 3,5-bis(t-butylthio) chlorobenzene. The yield was 79% based on the a theoretical amount.

Second Step

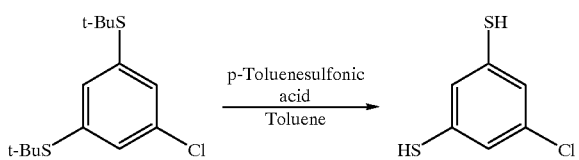

In the same manner as that in the second step of Example 17 except for adding 28.9 parts of 3,5-bis(t-butylthio)-chlorobenzene obtained in the first step in place of 3,5-dichlorophenyl-t-butylsulfide, under reflux for 12 hours and changing the amount of a 10% aqueous sodium hydroxide solution (400 parts) to be added after separating liquids, the procedure was carried out and 16.5 parts of colorless needle crystals were obtained.

Melting point: 55° C.;

$^1$H-NMR (CDCl$_3$): δ7.03 (s, 3H), 3.47 (s, 2H)

As the result, the product was confirmed to be 5-chloro-1,3-benzenedithiol. The yield was 93% based on the theoretical amount.

Example 22

First Step

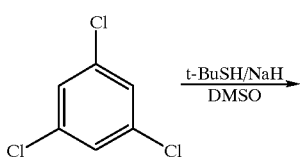

-continued

[Structure: 1,3,5-tris(t-butylthio)benzene]

The same procedure as that in the first step of Example 15 was carried out and 1,3,5-tris(t-butylthio)benzene was obtained.

Second Step

[Structure: 1,3,5-tris(t-butylthio)benzene] —Methanesulfonic acid / Xylene→ [Structure: 1,3,5-trimercaptobenzene]

In the reaction vessel used in the second step of Example 16 were charged, under nitrogen gas atmosphere, 34.3 parts of 1,3,5-tris(t-butylthio)benzene obtained as mentioned above, 100 parts of xylene and 9.6 parts of methanesulfonic acid, and the mixture was refluxed under heating for 7 hours while removing isobutylene formed by passing a nitrogen gas thereinto. Subsequently, 500 parts of toluene were added dropwise to the mixture under heating to reflux said toluene for 5 hours while a part thereof was removed and isobutylene was completely removed. Then, the mixture was cooled to room temperature, and 100 parts of water were added thereto and the mixture was stirred and separated to collect the organic phase. To the organic phase were added 600 parts of a 10% aqueous sodium hydroxide solution and the resulting mixture was stirred and the aqueous phase was collected by separation of the liquids. Then, according to the same procedure as that in the second step of Example 17, 13.0 parts of colorless needle crystals were obtained.

Melting point: 56 to 59° C.;

$^1$H-NMR (CDCl$_3$): δ6.94 (s, 3H), 3.41 (s, 3H).

As the result, the product was confirmed to be 1,3,5-trimercaptobenzene. The yield was 75% based on the theoretical amount.

Example 23

First Step

[Structure: 1,3,5-trichlorobenzene] —Ph$_2$CHSH/NaOMe / DMSO→ [Structure: 3,5-dichlorophenyl(benzhydryl)sulfide]

In the same reaction vessel used in the first step of Example 17 were charged, under nitrogen atmosphere, 44.0 parts of diphenylmethanethiol, 200 parts of dimethylsulfoxide and 12.4 parts of sodium methoxide with a purity of 96%, and the mixture was stirred at 50° C. for 30 minutes.

Subsequently, 36.3 parts of 1,3,5-trichlorobenzene was added to the mixture, and then, in the same manner as that in the first step of Example 17 except for subjecting to the reaction at 80° C. for 3 hours, the procedure was carried out up to removal of toluene, then, a colorless oily residue was obtained. The residue was recrystallized from methanol and 64.8 parts of colorless platy crystals were obtained.

Melting point: 54° C.;

$^1$H-NMR (CDCl$_3$): δ7.40 (d, J=7.4 Hz, 4H), 7.31 (d, J=7.4 Hz, 4H), 7.24 (t, J=7.4 Hz, 2H), 7.09 (t, J=1.7 Hz, 1H), 7.06 (d, J=1.7 Hz, 2H), 5.56 (s, 1H).

As the result, the product was confirmed to be 3,5-dichlorophenyl(benzhydryl)sulfide. The yield was 94% based on the theoretical amount.

Second Step

[Structure: 3,5-dichlorophenyl(benzhydryl)sulfide] —p-Toluenesulfonic acid / Toluene→ [Structure: 3,5-dichlorothiophenol]

In the same manner as that in the second step of Example 17 except for adding 34.5 parts of 3,5-dichlorophenyl(benzhydryl)sulfide obtained in the first step in place of 3,5-dichlorophenyl-t-butylsulfide under reflux for 8 hours, the procedure was carried out, and when a pH of the mixture was adjusted to 2, crystals were precipitated. This precipitates were collected by filtration and 11.6 parts of white crystals were obtained.

Melting point: 62° C.;

$^1$H-NMR (CDCl$_3$): δ7.15 (s, 3H), 3.55 (s, 1H).

As the result, the product was confirmed to be 3,5-dichlorothiophenol. The yield was 65% based on the theoretical amount.

Example 24

First Step

[Structure: 1,3,5-trichlorobenzene] —t-BuSNa / DMSO→ [Structure: 3,5-dichlorophenyl-t-butylsulfide]

In the same reaction vessel used in the first step of Example 17 were charged, under nitrogen atmosphere, 22.4 parts of sodium t-butylmercaptide, 200 parts of dimethylsulfoxide and 36.3 parts of 1,3,5-trichlorobenzene, and the mixture was heated at 80° C. for 5 hours. Then, in the same manner as that in the first step of Example 17, the procedure was carried out and 37.8 parts of a colorless liquid with a boiling point of 75° C./0.4 Torr were obtained. The $^1$H-NMR (CDCl$_3$) of the resulting material was the same as those of the product obtained in the first step of Example 17.

As the result, the product was confirmed to be 3,5-dichlorophenyl-t-butylsulfide. The yield was 80% based on the theoretical amount.

Second Step

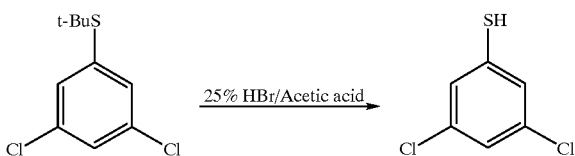

In an autoclave made of glass were charged, under nitrogen atmosphere, 23.5 parts of 3,5-dichlorophenyl-t-butylsulfide, and 161.8 parts of an acetic acid solution containing 25% of hydrogen bromide, and the mixture was stirred under reflux for 3 hours. Then, the reaction mixture was cooled to room temperature and transferred to another apparatus. After 150 parts of water and 100 parts of toluene were added to the mixture, followed by stirring, the mixture was allowed to stand and liquids were separated. When the same procedure as that in Example 17 was then carried out, crystals were precipitated. This precipitates were collected by filtration and 15.1 parts of white crystals were obtained.

Melting point: 62° C.;

$^1$H-NMR (CDCl$_3$): δ7.15 (s, 3H), 3.55 (s, 1H)

As the result, the product was confirmed to be 3,5-dichlorothiophenol. The yield was 84% based on the theoretical amount.

Example 25

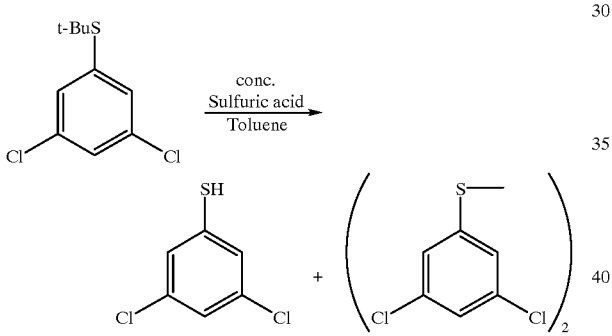

In the similar reaction vessel used in the second step of Example 16 were charged, under nitrogen atmosphere, 23.5 parts of 3,5-dichlorophenyl-t-butylsulfide obtained in the first step of Example 17, 10.3 parts of 95% conc. sulfuric acid and 50 parts of toluene, and the mixture was refluxed under heating for 3 hours while stirring. After cooling to room temperature, 150 parts of water and 50 parts of toluene were added to the reaction mixture and the resulting mixture was allowed to stand and liquids were separated. To the organic phase were added 200 parts of a 10% aqueous sodium hydroxide solution, the mixture was stirred and liquids were again separated. The organic phase separated was washed with a saturated saline solution and dehydrated over anhydrous sodium sulfate, and toluene was removed under reduced pressure and a pale yellowish liquid was obtained. This was treated with methanol and 8.8 parts of colorless needle crystals were obtained.

Melting point: 65° C.;

$^1$H-NMR (CDCl$_3$): δ7.33 (d, J=1.7 Hz, 4H), 7.23 (t, J=1.7 Hz, 2H).

As the result, the product obtained from the organic phase was confirmed to be bis(3,5-dichlorophenyl)disulfide. The yield was 49% based on the theoretical amount.

To the combined aqueous phases was added a 12N aqueous hydrochloric acid solution thereby the pH of the mixture was adjusted to 2, and the precipitated crystals were collected by filtration and 4.3 parts of colorless needle crystals were obtained.

Melting point: 62° C.;

$^1$H-NMR (CDCl$_3$): δ7.15 (s, 3H), 3.55 (s, 1H).

As the result, the product from the aqueous phase was confirmed to be 3,5-dichlorothiophenol. The yield was 24% based on the theoretical amount.

Example 26

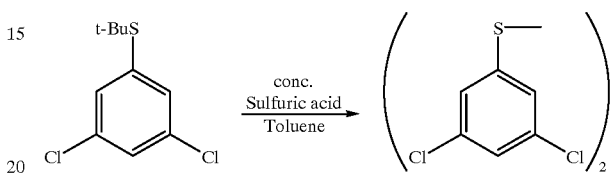

The similar reaction as that in Example 25 was carried out except for changing the amount of toluene to be used as a reaction solution (100 parts) and subjecting to reflux while removing water for 3 hours, and purification of the reaction product was carried out in the similar operations. From the organic phase, 12.9 parts of colorless needle crystals having a melting point of 65° C. were obtained. The $^1$H-NMR was well agreed with the $^1$H-NMR of the crystals obtained from the organic phase of Example 25. From the fact, the product from the organic phase was confirmed to be bis(3,5-dichlorophenyl)disulfide. The yield was 72% based on the theoretical amount.

From the combined aqueous phases, 0.4 part of colorless needle crystals having a melting point of 62° C. was obtained. Similarly, the product was confirmed to be 3,5-dichlorothiophenol from the $^1$H-NMR. The yield was 2% based on the theoretical amount.

Example 27

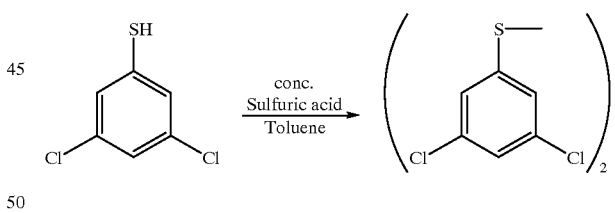

In the similar reaction vessel used in the second step of Example 16 were charged, under nitrogen atmosphere, 17.9 parts of 3,5-dichlorothiophenol obtained in Example 1, 20.7 parts of 95% sulfuric acid and 100 parts of toluene, and the mixture was refluxed while removing water for 6 hours. After cooling to room temperature and stirring the mixture by addition of 150 parts of water, the resulting mixture was allowed to stand and liquids were separated. To the organic phase were added 200 parts of a 10% aqueous sodium hydroxide solution and the mixture was stirred, then, the mixture was allowed to stand. The organic phase collected by separating liquids was washed with a saturated saline solution and dehydrated over anhydrous sodium sulfate. Toluene was removed under reduced pressure and 17.5 parts of colorless needle crystals were obtained.

Melting point: 65° C.;

$^1$H-NMR (CDCl$_3$): δ7.33 (d, J=1.7 Hz, 4H), 7.23 (t, J=1.7 Hz, 2H)

As the result, the product from the organic phase was confirmed to be bis(3,5-dichlorophenyl)disulfide. The yield was 98% based on the theoretical amount.

Example 28

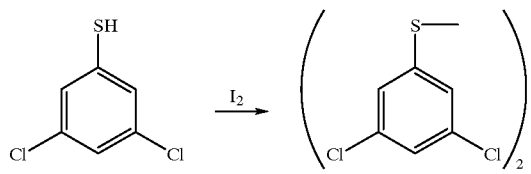

In the similar reaction vessel used in Example 1 were charged 17.9 parts of 3,5-dichlorothiophenol obtained in Example 1, 50 parts of toluene and 50 parts of water. After uniformly dispersing the mixture, a solution of 12.7 parts of iodine in 30 parts of toluene was added dropwise to the mixture. After stirring the resulting mixture at room temperature for 30 minutes, the mixture was allowed to stand and the organic phase was obtained by separating liquids. The organic phase was washed successively with a 5% aqueous sodium thiosulfate and a saturated saline solution, and dehydrated over anhydrous sodium sulfate. Toluene was removed under reduced pressure and 17.3 parts of colorless needle crystals were obtained.

Melting point: 65° C.;
$^1$H-NMR (CDCl$_3$): δ7.33 (d, J=1.7 Hz, 4H), 7.23 (t, J=1.7 Hz, 2H).

As the result, the product from the organic phase was confirmed to be bis(3,5-dichlorophenyl)disulfide. The yield was 98% based on the theoretical amount.

What is claimed is:

1. A process for the preparation of an aromatic thiol represented by the formula (I):

wherein Ar is an aromatic hydrocarbon ring;
Y represents at least one substituent bonded to a carbon atom constituting the aromatic hydrocarbon ring of Ar, said substituent being selected from the group consisting of halogen, nitro, nitrile, sulfone, sulfamoyl and hydrocarbylsulfonyl groups; m is an integer of 1 or more; and n is an integer of 1 or more, which comprises (a) reacting an aromatic thioether represented by the formula (II):

wherein R represents an aliphatic or aromatic monovalent tertiary hydrocarbyl group represented by the formula (VII):

(VII)

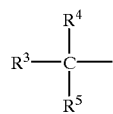

wherein R$^3$, R$^4$ and R$^5$ each represents an alkyl or aryl group, or a monovalent dialkyl, monovalent diaryl or monoalkylmonoaryl secondary hydrocarbyl group, wherein Y, Ar, m and n have the same meanings as defined above;
with (A) at least one Lewis acid selected from the group consisting of boron trifluoride, boron trichloride, boron tribromide, aluminum chloride, titanium tetrachloride, ferric chloride, tin tetrachloride, antimony pentoxide and boron trifluoride-diethyl ether complex, in the presence of a solvent, or with at least one protonic acid selected from the group consisting of benzenesulfonic acid, p-toluenesulfonic acid and methanesulfonic acid; and (b) optionally hydrolyzing the obtained reaction product from step (a).

2. The process according to claim 1, wherein Ar is a benzene ring, and (A) is a Lewis acid.

3. The process according to claim 1, wherein Y is a chloro atom, n is 2 and m is 1.

4. The process according to claim 1, wherein (A) is the Lewis acid and is at least one selected from the group consisting of boron tribromide, aluminum chloride, titanium tetrachloride and ferric chloride.

5. The process according to claim 1, wherein (A) is said Lewis acid in an amount of 0.01 to 3 mol per mol of the aromatic thioether.

6. The process according to claim 5, wherein the Lewis acid is used in an amount of 0.02 to 1.1 mol per mol of the aromatic thioether.

7. The process according to claim 1, wherein Ar is a benzene ring, and (A) is a protonic acid.

8. A process for the preparation of an aromatic disulfide represented by the formula (III):

wherein Ar is an aromatic hydrocarbon ring;
Y represents at least one substituent bonded to a carbon atom constituting the aromatic hydrocarbon ring of Ar, said substituent being selected from the group consisting of halogen, nitro, nitrile, sulfone, sulfamoyl and hydrocarbylsulfonyl groups;
n is an integer of 1 or more;
which comprises (a) producing an aromatic thiol represented by the formula (I)

wherein Y, Ar and n are defined above and m is 1, by a process which comprises reacting an aromatic thioether represented by the formula (II):

wherein R represents an aliphatic or aromatic monovalent tertiary hydrocarbyl group represented by the formula (VII):

(VII)

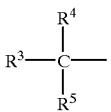

wherein R$^3$, R$^4$ and R$^5$ each represents an alkyl or aryl group, or a monovalent dialkyl, monovalent diaryl or monoalkylmonoaryl secondary hydrocarbyl group, wherein Y, Ar, m and n have the same meanings as defined above;
with (A) concentrated sulfuric acid or at least one Lewis acid selected from the group consisting of boron trifluoride, boron trichloride, boron tribromide, aluminum chloride, titanium tetrachloride, ferric chloride, tin tetrachloride, antimony pentoxide and boron trifluoride-diethyl ether complex, in the presence of a solvent and (b) oxidizing said aromatic thiol without isolation to produce the aromatic disulfide represented by the formula (III).

9. A process for the preparation of an aromatic thiol represented by the formula (I):

$$Y_n\text{—Ar—}(SH)_m \qquad (I)$$

wherein Ar is an aromatic hydrocarbon ring;
Y represents at least one substituent bonded to a carbon atom constituting the aromatic hydrocarbon ring of Ar, said substituent being selected from the group consisting of halogen, nitro, nitrile, sulfone, sulfamoyl and hydrocarbylsulfonyl groups; m is an integer of 1 or more; and n is an integer of 1 or more,
which comprises
(i) reacting (B) an aromatic halogen compound represented by the formula (IV):

$$Y_n\text{—Ar—}X_m \qquad (IV)$$

wherein Ar and Y have the same meanings as defined above;
X represents a halogen group bonded to a carbon atom constituting the aromatic hydrocarbon ring of Ar;
m is an integer of 1 or more; and
n is an integer of 1 or more,
with (C)(1) a hydrocarbylmercaptide alkali metal salt represented by the formula (V):

$$RSM \qquad (V)$$

wherein R is an aliphatic or aromatic monovalent tertiary hydrocarbyl group represented by the formula (VII):

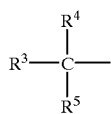

(VII)

wherein $R^3$, $R^4$ and $R^5$ each represents an alkyl group or an aryl group, or a monovalent dialkyl, monovalent diaryl or monoalkylmonoaryl secondary hydrocarbyl group; and
M represents an alkali metal; and/or (C)(2)(a) a hydrocarbyl mercaptan represented by the formula (VI):

$$RSH \qquad (VI)$$

wherein R has the same meaning as defined above, and (C)(2)(b) an alkali metal, or a hydroxide, carbonate, hydride or alkoxide thereof in the presence of (D) an aprotic polar solvent to produce an aromatic thioether represented by the formula (II):

$$Y_n\text{—Ar—}(SR)_m \qquad (II)$$

wherein Y, Ar and R have the same meanings as defined above; m is an integer of 1 or more; and n is an integer of 1 or more; and
(ii) reacting the resulting aromatic thioether from step (i) with (A) a Lewis acid selected from the group consisting of boron trifluoride, boron trichloride, boron tribromide, aluminum chloride, titanium tetrachloride, ferric chloride, tin tetrachloride, antimony pentoxide and boron trifluoride-diethyl ether complex, in the presence of a solvent, or with a protonic acid, and
(iii) optionally hydrolyzing the obtained reaction product from step (ii).

10. The process according to claim 9, wherein Ar is a benzene ring and (A) is a Lewis acid.

11. The process according to claim 9, wherein Y is chloro, n is 2 and m is 1.

12. The process according to claim 9, wherein the Lewis acid is at least one selected from the group consisting of boron tribromide, aluminum chloride, titanium tetrachloride and ferric chloride.

13. The process according to claim 8, wherein (A) is said Lewis acid in an amount of 0.01 to 3 mol per mol of the aromatic thioether.

14. The process according to claim 13, wherein the Lewis acid is used in an amount of 0.02 to 1.1 mol per mol of the aromatic thioether.

15. The process according to claim 9, wherein Ar is a benzene ring, and (A) is a protonic acid.

16. The process according to claim 9, wherein (A) is the protonic acid and is at least one acid selected from the group consisting of hydrofluoric acid, hydrochloric acid, hydrobromic acid, hydrogen bromide-acetic acid, sulfuric acid, benzenesulfonic acid, p-toluenesulfonic acid and methanesulfonic acid.

17. The process according to claim 16, wherein the protonic acid is at least one selected from the group consisting of p-toluenesulfonic acid and methanesulfonic acid.

18. The process according to claim 15, wherein the protonic acid is used in an amount of 0.1 to 5 mol per mol of the aromatic thioether.

19. The process according to claim 9, wherein Ar is a benzene ring and X is a chlorine atom.

20. The process according to claim 9, wherein the aromatic halogen compound (B) is reacted with (C)(2)(a) the hydrocarbyl mercaptan represented by the formula (VI) and (C)(2)(b) the alkali metal, hydroxide, carbonate, hydride or alkoxide thereof.

21. The process according to claim 2, wherein Y is a chloro atom, n is 2 and m is 1.

22. The process according to claim 2, wherein the Lewis acid is at least one selected from the group consisting of boron tribromide, aluminum chloride, titanium tetrachloride and ferric chloride.

23. The process according to claim 22, wherein the Lewis acid is in an amount of 0.01 to 3 mol per mol of the aromatic thioether.

24. The process according to claim 23, wherein the Lewis acid is in an amount of 0.02 to 0.1 mol per mol of the aromatic thioether.

25. The process according to claim 10, wherein Y is chloro, n is 2 and m is 1.

26. The process according to claim 10, wherein the Lewis acid is at least one selected from the group consisting of boron tribromide, aluminum chloride, titanium tetrachloride and ferric chloride.

27. The process according to claim 11, wherein (A) is the Lewis acid and is at least one selected from the group consisting of boron tribromide, aluminum chloride, titanium tetrachloride and ferric chloride.

28. The process according to claim 1, wherein (A) is a Lewis acid and the process is carried out at a temperature of room temperature to 200° C., or (A) is a protonic acid and the process is carried out at a temperature of 100 to 200° C.

29. The process according to claim 1, wherein (A) is said protonic acid.

30. The process according to claim 9, wherein (A) is said protonic acid.

* * * * *